United States Patent
Yoshida

(10) Patent No.: US 9,839,228 B2
(45) Date of Patent: Dec. 12, 2017

(54) VOLATILE DISINFECTANT

(71) Applicant: E-TECH CO., LTD, Hyogo (JP)

(72) Inventor: Eiichi Yoshida, Hyogo (JP)

(73) Assignee: E-TECH CO., LTD, Kobe-shi, Hyogo (JP)

( * ) Notice: Subject to any disclaimer, the term of this patent is extended or adjusted under 35 U.S.C. 154(b) by 0 days.

(21) Appl. No.: 14/911,489

(22) PCT Filed: Sep. 7, 2014

(86) PCT No.: PCT/JP2014/073591
§ 371 (c)(1),
(2) Date: Feb. 11, 2016

(87) PCT Pub. No.: WO2015/034072
PCT Pub. Date: Mar. 12, 2015

(65) Prior Publication Data
US 2016/0198720 A1    Jul. 14, 2016

(30) Foreign Application Priority Data
Sep. 8, 2013    (JP) ................. 2013-185798

(51) Int. Cl.
*A01N 25/02*    (2006.01)
*A23L 3/3463*    (2006.01)
(Continued)

(52) U.S. Cl.
CPC ............ *A23L 3/3463* (2013.01); *A01N 59/00* (2013.01); *A23L 3/358* (2013.01)

(58) Field of Classification Search
None
See application file for complete search history.

(56) References Cited

U.S. PATENT DOCUMENTS 3,775,503 A    11/1973    Driscoll et al.
4,451,480 A *  5/1984    DeVillez .............. C07D 323/02
                                                        514/463

(Continued)

FOREIGN PATENT DOCUMENTS

FR    2100865 A    3/1972
JP    10-130173 A    5/1998
(Continued)

OTHER PUBLICATIONS

O'Lenick, Anthony J.; "Basic Silicone Chemistry—A Review," 2009, Silicone Spectator, pp. 1-23.*
(Continued)

*Primary Examiner* — Devang K Thakor
*Assistant Examiner* — Ivan A Greene
(74) *Attorney, Agent, or Firm* — Yokoi & Co., U.S.A.; Toshiyuki Yokoi

(57) ABSTRACT

This can provide a volatile disinfectant produced by bubbling ozone gas into a volatile solvent, the volatile solvent containing at least one volatile liquid paraffin, one volatile silicone oil, or a mixture thereof as a base under stirring the volatile solvent to thereby allow the volatile solvent to contain the ozone gas, the volatile disinfectant characterized in that, when applied to an object, the volatile disinfectant inactivates pathogens on the object and then volatilizes from the object.

2 Claims, 7 Drawing Sheets

(51) Int. Cl.
*A01N 59/00* (2006.01)
*A23L 3/358* (2006.01)

(56) References Cited

U.S. PATENT DOCUMENTS

| | | | |
|---|---|---|---|
| 5,103,061 A | 4/1992 | Blackborow et al. | |
| 5,155,531 A * | 10/1992 | Kurotori | G03G 15/107 399/250 |
| 5,503,681 A * | 4/1996 | Inada | B01D 12/00 134/1 |
| 5,830,488 A * | 11/1998 | Suzuki | A01N 31/02 424/401 |
| 5,851,674 A * | 12/1998 | Pellerite | B82Y 30/00 204/192.26 |
| 6,312,759 B1 * | 11/2001 | Yamada | C07C 17/23 134/42 |
| 6,372,700 B1 * | 4/2002 | Zazerra | C11D 3/3947 252/364 |
| 2005/0226944 A1 * | 10/2005 | Bertha | A61K 47/44 424/731 |
| 2005/0276723 A1 * | 12/2005 | Sundaram | A01N 59/00 422/28 |
| 2009/0117055 A1 * | 5/2009 | Ryu | A01N 59/00 424/43 |

FOREIGN PATENT DOCUMENTS

| | | |
|---|---|---|
| JP | 10-139645 A | 5/1998 |
| JP | 2000-086408 A | 3/2000 |
| JP | 2006-089388 A | 4/2006 |
| JP | 2008-297270 A | 12/2008 |
| JP | 2009-525974 A | 7/2009 |
| JP | 2013-234132 A | 11/2013 |

OTHER PUBLICATIONS

Sinko, Patrick J.; Martin's Physical Pharmacy and Pharmaceutical Sciences, 5th ed., 2006; Lippincott Williams & Wilkins, Chapter 10, pp. 231-265.*
Kirk-Othmer Encyclopedia of Chemical Technology entry for "ozone" and "disinfection", 2000; John Wiley & Sons; vol. 8, pp. 605-672 and vol. 17, pp. 768-822.*
Soltrol® 100 Isoparaffin Solvent Safety Data Sheet (pp. 1-13, as provided).*
International Search Report dated Nov. 18, 2014 from corresponding International Patent Application No. PCT/JP2014/073591; 1 pg.
Office action dated Aug. 22, 2014 from corresponding Japanse Patent Application No. 2014-137267; 18 pgs.
Extended European Search Report dated Mar. 3, 2017.

* cited by examiner

FIG. 2

| | sterilization test | | | | | | | drying test |
|---|---|---|---|---|---|---|---|---|
| | Bacillus subtilis | | | | Bacillus coli | Staphylococcus aureus | Pseudomonas aeruginosa | Candida tropicalis | |
| | time point of production completion | | time point after one month passed | | producing completion point | producing completion point | producing completion point | producing completion point | |
| | 1 minute | 5 minutes | 1 minute | 5 minutes | 5 minutes | 5 minutes | 5 minutes | 20 minutes | |
| Example 1 | — | — | — | — | — | — | — | — | volatile |
| Example 2 | — | — | — | — | — | — | — | — | volatile |
| Example 3 | — | — | — | — | — | — | — | — | volatile |
| Example 4 | — | — | — | — | — | — | — | — | volatile |
| Example 5 | — | — | — | — | — | — | — | — | volatile |
| Example 6 | — | — | — | — | — | — | — | — | volatile |
| Example 7 | — | — | — | — | — | — | — | — | volatile |
| Example 8 | — | — | — | — | — | — | — | — | volatile |
| Example 9 | — | — | — | — | — | — | — | — | volatile |
| Comparison Example 1 | — | — | | | | | | | non-volatile |
| Comparison Example 2 | — | — | | | | | | | non-volatile |

FIG. 3
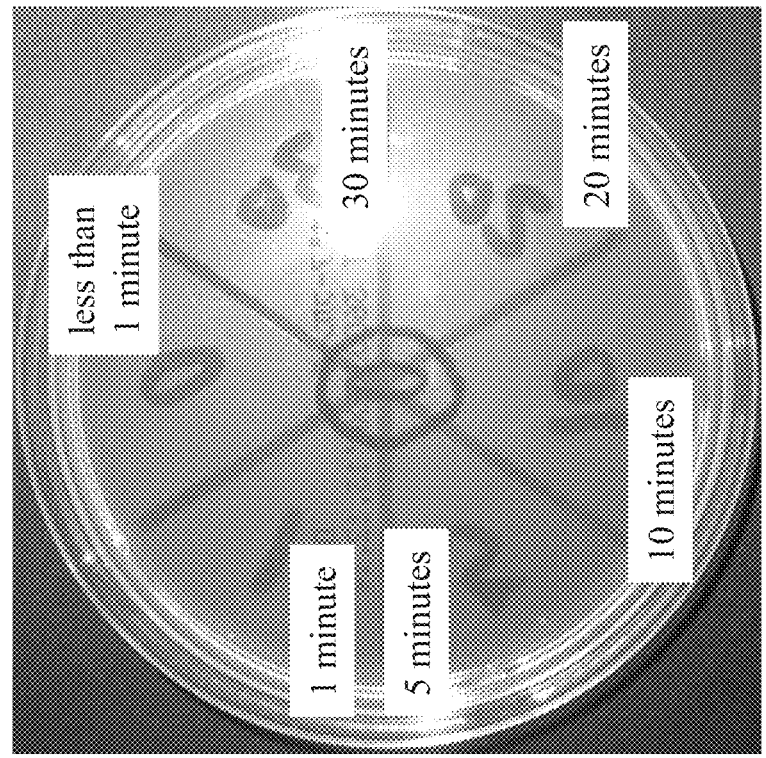
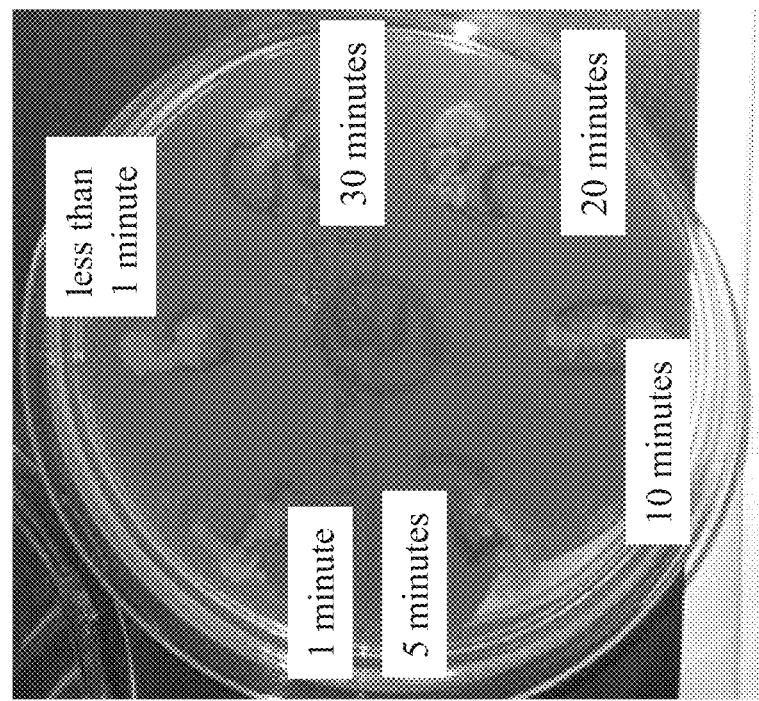

VOLATILE DISINFECTANT

CROSS REFERENCE TO RELATED APPLICATIONS

This application claims priority to Japanese Patent Application No. 2013-185798 filed on Sep. 8, 2013, the entire contents of which are incorporated by reference herein. This application is a U.S. nationalization under 35 U.S.C. .sctn. 371 of International Application No. PCT/JP2014/073591, filed Sep. 7, 2014. The disclosure set forth in the referenced application is incorporated herein by reference in its entirety.

TECHNICAL FIELD

The present invention relates to a volatile disinfectant and a method for producing a volatile disinfectant.

BACKGROUND ART

Conventionally, techniques of a volatile disinfectant exist a lot. For examples, Japanese Unexamined Patent Application Publication No. 10-130173 (Patent Literature 1) discloses quick-drying disinfectant obtained by combining sterilization disinfectant with adhesive, the sterilization disinfectant consisting of combinations of carboxy vinyl polymers, natural polysaccharides and/or derivative, fatty acid ester and lower alcohol. Japanese Unexamined Patent Application Publication No. 2000-86408 (Patent Literature 2) discloses quick-drying finger disinfectant containing alcohol solution. Japanese Unexamined Patent Application Publication No. 2006-89388 (Patent Literature 3) discloses quick-drying germicide obtained by combining alcohol with an acetylated sodium hyaluronate, the quick-drying germicide having excellent skin protection and moisture retaining effects. Japanese Unexamined Patent Application Publication No. 2008-297270 (Patent Literature 4) discloses quick-drying disinfectant containing alcohol and two kinds of oxide.

In techniques of non-volatile disinfectant, Japanese Unexamined Patent Application Publication No. 10-139645 (Patent Literature 5) discloses an ozone enclosure viscous body and a generation device, the ozone enclosure viscous body obtained by enclosing ozone gas for high viscosity material.

By the way, Japanese Unexamined Patent Application Publication (Translation of PCT Application) No. 2009-525974 (Patent Literature 6) that this inventor invented earlier discloses a disinfectant having ozone, the disinfectant characterized in that the disinfectant has been given sterilizing power by stirring a liquid paraffin or a vaseline under mixing ozone, to thereby contain ozone. Japanese Unexamined Patent Application Publication No. 2013-234132 (Patent Literature 7) that this inventor invented earlier discloses silicone oil having ozone, the silicone oil characterized in that the silicone oil has been given sterilizing power by stirring silicone oil under bubbling ozone as bubbles into the silicone oil to thereby contain ozone as microbubbles in the silicone oil.

PRIOR ART DOCUMENTS

Patent Literature

Patent Literature 1: Japanese Unexamined Patent Application Publication No. 10-130173
Patent Literature 2: Japanese Unexamined Patent Application Publication No. 2000-86408
Patent Literature 3: Japanese Unexamined Patent Application Publication No. 2006-89388
Patent Literature 4: Japanese Unexamined Patent Application Publication No. 2008-297270
Patent Literature 5: Japanese Unexamined Patent Application Publication No. 10-139645
Patent Literature 6: Japanese Unexamined Patent Application Publication (Translation of PCT Application) No. 2009-525974
Patent Literature 7: Japanese Unexamined Patent Application Publication No. 2013-234132

SUMMARY OF INVENTION

Problems to be Solved by the Invention

However, the techniques mentioned in Patent Literature 1-4 have a problem that the sterilizing property is still insufficient. The techniques mentioned in Patent Literature 5 have a problem that the disinfectant has no volatility.

Meanwhile, as shown in Patent Literature 6, 7, the inventor invented the disinfectant containing ozone gas, the disinfectant having a strong sterilizing property with liquid paraffin or silicone oil that is no reaction to ozone gas. The disinfectant is used by a liquid paraffin or a silicone oil as a solvent, the solvent of a liquid paraffin or a silicone oil is usually non-volatile. Therefore, after applying the disinfectant to an object and sterilizing the object, the solvent remains on the object.

Here, the liquid paraffin or the silicone oil has a function as a lubricating oil, for a medical appliance and a dental appliance requiring sterilization and lubrication, it is possible to use preferably the disinfectant containing the liquid paraffin or the silicone oil as a solvent.

Meanwhile, when the solvent remains after application of the disinfectant on a medical appliance requiring only sterilization, such as blood dialysis apparatus, it is necessary to perform post-processing to wash away the remaining solvent with water, etc. and there is a problem that it takes user's labor and time. The problem that the solvent remains after application of the disinfectant interferes with the development of the disinfectant to a medical field, a sanitary field, a food field, etc.

Accordingly, the present invention was created as a solution for the problems and aims at providing a volatile disinfectant and a method for producing a volatile disinfectant, which can inactivate even a high durable pathogen, make a post-processing after the application unnecessary, and improve the safety for a user to treat.

Solution to Problem

After conducting rigorous and repeated research, the present inventors have completed a novel volatile disinfectant and a novel method for producing a volatile disinfectant in accordance with the present invention. Namely, the present invention comprises a volatile disinfectant, the volatile disinfectant produced by bubbling ozone gas into a volatile solvent, the volatile solvent containing at least one volatile liquid paraffin selected from the group consisting of a light liquid isoparaffin, a light isoparaffin, and a hydrogenated polyisobutene, one volatile silicone oil consisting of a cyclic dimethyl silicone oil, or a mixture thereof as a base under stirring the volatile solvent to thereby allow the volatile solvent to contain the ozone gas, the volatile disinfectant characterized in that, when the volatile disinfectant applied to an object, the volatile disinfectant inactivates pathogens on the object and then volatilizes from the object. The concentration of the base is in a range from 50 volume % to 100 volume % based upon the total volume of the volatile solvent.

Also, the present invention comprises a method for producing a volatile disinfectant, the method comprising a step of bubbling ozone gas into a volatile solvent, the volatile solvent containing at least one volatile liquid paraffin selected from the group consisting of a light liquid isoparaffin, a light isoparaffin, and a hydrogenated polyisobutene, one volatile silicone oil consisting of a cyclic dimethyl silicone oil, or a mixture thereof as a base, and a step of stirring the volatile solvent bubbled ozone gas to thereby allow the volatile solvent to contain the ozone gas, the method characterized by producing the volatile disinfectant, when the volatile disinfectant applied to an object, the volatile disinfectant inactivating pathogens on the object and then volatilizes from the object.

Advantageous Effects of Invention

According to the present invention, a volatile disinfectant and a method for producing a volatile disinfectant can inactivate high durable pathogens, make a post-processing after the application unnecessary, and improve the safety for user to treat.

BRIEF DESCRIPTION OF DRAWINGS

FIG. 2 is a sterilization test result and a drying test result in accordance with Examples 1-9 and Comparison Examples 1, 2.

FIG. 3A is a photograph indicating an agar medium after the culture when only a volatile liquid paraffin was contacted with a diluent of *Bacillus subtilis* for less than 1 minute, 1 minute, 5 minutes, 10 minutes, 20 minutes, or 30 minutes.

FIG. 3B is a photograph indicating an agar medium after the culture when a volatile disinfectant of Example 1 was contacted with a diluent of *Bacillus subtilis* for less than 1 minute, 1 minute, 5 minutes, 10 minutes, 20 minutes, or 30 minutes.

FIG. 6A is a photograph indicating a test panel of the time point when a volatile disinfectant of Example 1 was dropped on.

FIG. 6B is a photograph indicating a test panel of the time point when it passed for a few minutes after a volatile disinfectant of Example 1 was dropped on.

DETAILED DESCRIPTION

Figure 1:
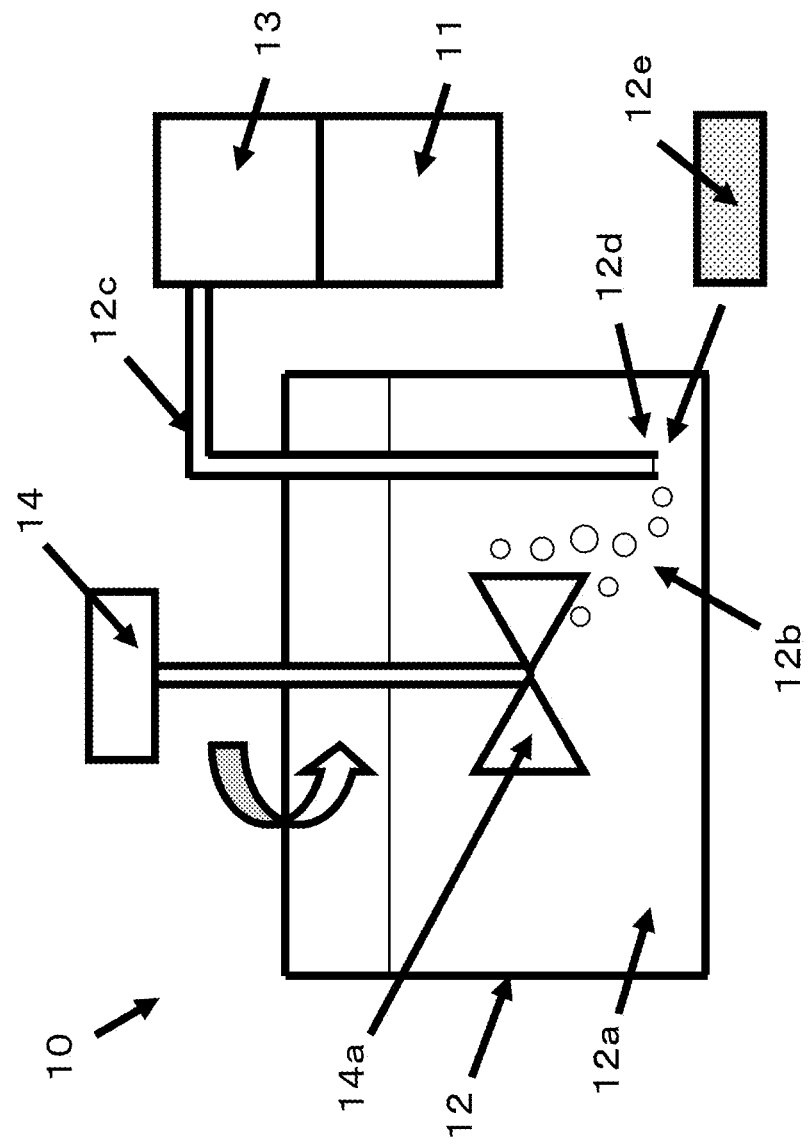
FIG. 1 is an illustration indicating an example of a manufacturing apparatus of a volatile disinfectant in accordance with an embodiment of the present invention.

The preferred embodiments of a volatile disinfectant and a method for producing a volatile disinfectant in the present invention will be explained below according to the attached drawings; thereby the present invention will be clearly understood. The embodiments below are examples materializing the present invention, and do not limit the technical scope of the present invention.

<Volatile Disinfectant>

The present invention comprises a volatile disinfectant, the volatile disinfectant produced by bubbling ozone gas into a volatile solvent, the volatile solvent containing at least one volatile liquid paraffin selected from the group consisting of a light liquid isoparaffin, a light isoparaffin, and a hydrogenated polyisobutene, one volatile silicone oil consisting of a cyclic dimethyl silicone oil, or a mixture thereof as a base under stirring the volatile solvent to thereby allow the volatile solvent to contain the ozone gas, the volatile disinfectant characterized in that, when the volatile disinfectant applied to an object, the volatile disinfectant inactivates pathogens on the object and then volatilizes from the object.

Conventionally, ozone gas is known by having a very strong sterilizing property, and the sterilizing property is caused by the destruction of the cell membrane or the nucleic acid of a bacteria. Therefore, the ozone gas can make every bacteria including a high durable spore forming bacteria inactivate (deaden) in comparison with a general disinfectant or an antibiotic. And, ozone gas has characteristic that the ozone gas does not generate a resistant bacteria. The bacteria being inactivated target can include a Gram negative bacteria, a Gram-negative *bacillus*, a Gram positive bacteria, a Gram-positive *bacillus*, etc. except a spore forming bacteria. The bacteria can include *Bacillus subtilis, Bacillus coli, Staphylococcus aureus, Pseudomonas aeruginosa, Klebsiella pneumoniae, Staphylococcus epidermidis*, methicillin-resistant *Staphylococcus aureus* (MRSA), methicillin-sensitive *Staphylococcus aureus* (MSSA), *Candida albicans, Helicobacter pylori*, tuberculosis, *Diphtheria bacteria, Bacillus coli* O-157 (enterohemorrhagic *Escherichia coli*), *Vibrio cholerae*, Sarumorera fungus, etc. The ozone gas can inactivate a pathogen such as a Fungi (molds), an Acid-fast bacteria, a Virus, a Parasite, an Amoeba, etc. except the bacteria. The pathogen can include *Candida albicans, Candida tropicalis, Candida glabrata, Aspergillus niger, Aspergillus fumigatus, Aspergillus flavus*, Norovirus, Influenza virus, Avian influenza virus, etc. And the pathogen include the bacteria.

Meanwhile, the volatile liquid paraffin and the volatile silicone oil are hydrophobic such as a non-volatile liquid paraffin and non-volatile silicone oil, and are stable for ozone gas (not oxidized). The volatile liquid paraffin (the boiling point is approximately 170 .degree. C.) and the volatile silicone oil (the boiling point is approximately 170 .degree. C.-200 .degree. C.) are different from the non-volatile liquid paraffin and the non-volatile silicone oil, and are characterized by volatilizing and drying when be exposed to an atmosphere and left for a while. Then, the SP value ((cal/cm3) ½) (6.5-7.5) of the volatile liquid paraffin is partially overlapping the SP value ((cal/cm3) ½) (6.5-9.5) of the volatile silicone oil, the volatile liquid paraffin is mixed equally with the volatile silicone oil without reacting. Because the SP value ((cal/cm3) ½) of ozone gas is 14.5, the ozone gas does not have compatibility with the volatile liquid paraffin, the volatile silicone oil, or a mixture thereof. Here, the SP value ((cal/cm3) ½) is defined as evaporation energy/molar capacity ½, is a parameter to reflect the cohesive power of the material, and two solvents that the SP values are close or overlap each other mean that the compatibility is good. The above-mentioned SP value is an estimate value by the Fedors method.

So, the present invention comprises the volatile solvent containing the volatile liquid paraffin, the volatile silicone oil, or the mixture thereof as a base (stability base), and allows the volatile solvent to contain the ozone gas. In this way, it is possible to maintain the ozone gas into the volatile solvent without losing the sterilizing property of the ozone gas. When the volatile disinfectant is applied to a predetermined object, at first the ozone gas in the volatile solvent inactivates every bacteria, fungi, pathogen of the virus that exists on the object, and sterilizes, pasteurizes, and disinfects. Then, the boiling point of the volatile solvent is in a range from 170 .degree. C. to 200 .degree. C., the volatile disinfectant never volatilizes until the inactivation of bacteria by the ozone gas is completed. Next, when the volatile disinfectant is left for a while after the application to the object, the volatile solvent volatilizes (evaporates), diffuses into the atmosphere, and the volatile disinfectant is lost all from the object. Therefore, the user can inactivate pathogens existing on the object, it makes a post-processing after the application unnecessary, and it is possible to reduce user's labor and time.

The surface tension of the volatile liquid paraffin and the volatile silicone oil are small compared with the surface tension of water, etc. Therefore, the volatile disinfectant applied to the object easily penetrates to the details of the object, carrying the ozone gas to every corner, and it is possible to sterilize the object everywhere.

The volatile liquid paraffin and the volatile silicone oil are used for cosmetics, food additives, etc., even if the user sucks these, it is harmless to the human body. Then, when the ozone gas is a low concentration, even if the user sucks this, it is harmless to the human body. In addition, the ozone gas is authorized as food additive in Food and Drug Administration (FDA) of US. Therefore, the volatile disinfectant does not damage the health of the user to treat, and it is possible to improve the safety for the user.

In particular, among the conventional disinfectants, a high level disinfectant to inactivate a high durable pathogen is Glutaral, Futararu, and Peracetic acid, and all are toxic, poison, and powerful drug. Therefore the object after being disinfected with the high-level disinfectant must be thoroughly washed with water. The amount of water required for the water washing is usually large. And, if the user sucks the component of the high level disinfectant during the post-processing, it is possible to damage the health of the user. Although the volatile disinfectant has a strong sterilizing power that can be opposed to the high level disinfectants, the safety of the volatile disinfectant for the user is extremely high. The indication of the safety of the volatile disinfectant can include an oral cavity mucous membrane irritation, an acute oral toxicity (single dose toxicity), a skin irritation, an eye irritation, etc.

The volatile liquid paraffin and the volatile silicone oil hardly react with the ozone gas, for example, when the volatile disinfectant is stored by sealing, it is possible to keep the ozone gas in the long term without the ozone gas inactivating (oxidizing).

Therefore, it is possible to preferably use the volatile disinfectant for the sterilization, the pasteurization, and the disinfection to an object requiring only sterilization in a medical field, a sanitary field, a food field, an agriculture field, a dairy farming field, or the like.

Here, the kind of the ozone gas is not limited in particular. For example, the ozone gas can include a mixture gas of ozone gas and oxygen gas, a single gas of ozone gas alone, etc. About the mixing ratio of the ozone gas and oxygen gas in the mixture gas, for example, the mixing ratio of the ozone gas is in a range from 50 wt % to 2 wt %, and the mixing ratio of the oxygen gas is in a range from 50 wt % to 98 wt %.

The concentration of the ozone gas in the volatile solvent is not limited in particular. For example, in the point of the certainty of the sterilizing property and the safety to the human body, the concentration is preferably in a range from 0.1 ppm to 100.0 ppm based upon the volatile solvent, and is more preferably in a range from 1.0 ppm to 50.0 ppm based upon the volatile solvent. Here, the legal exposure regulation (working environment allowable concentration) exists that the concentration of the ozone gas in an atmosphere is less than 0.1 ppm. By making the concentration of the ozone gas in the volatile solvent be in the mentioned range, the concentration of the ozone gas in the atmosphere, the ozone gas volatilizing with the volatile solvent is allowed to the mentioned range of the legal exposure regulation, and it is possible to ensure the safety of the human body.

The kind of the volatile liquid paraffin of the base is not limited in particular. At least one volatile liquid paraffin is selected from the group consisting of a light liquid isoparaffin, a light isoparaffin, and a hydrogenated polyisobutene. For example, the light liquid isoparaffin includes isododecane, isohexadecane, etc. The kind of the volatile silicone oil of the base is not limited in particular. The volatile silicone oil includes a cyclic dimethylsilicone oil, and may include a linear dimethyl silicone oil, a branched silicone oil, a dimethicone, and modified silicone oil. The constitution of the volatile liquid paraffin is not limited in particular. The volatile liquid paraffin may comprise a kind of the volatile liquid paraffin, or a mixture of two or more volatile liquid paraffin. The volatile liquid paraffin described in the specification includes these both meanings. The volatile silicone oil is handled in the same way as the volatile liquid paraffin. In addition, the volatile solvent described in the specification means the solvent volatilizing from the object when a predetermined drying time passes after the solvent is applied to a predetermined object. When the weight of the solvent at the time point of the application is 100%, the drying time when the weight (drying weight, or percentage) of the solvent remaining in the object becomes approximately 0% is called the complete drying time.

The constitution of the mixture of the volatile liquid paraffin and the volatile silicone oil is not limited in particular. The complete drying time (complete volatilizing time) of the volatile liquid paraffin is usually shorter than the complete drying time of the volatile silicone oil, for example. When it is desired to shorten the complete drying time of the volatile disinfectant by using the mixture as the base, the concentration (mixing ratio) of the volatile liquid paraffin based upon the total mixture may be higher than the concentration of the volatile silicone oil. When it is desired to lengthen the complete drying time of the volatile disinfectant by using the mixture as the base, the concentration of the volatile liquid paraffin based upon the total mixture may be lower than the concentration of the volatile silicone oil.

The viscosity of the base is not limited in particular, for example, the viscosity at 25 .degree. C. is preferably in a range from 1 mPa s to 100 mPa s. And, the density of the base is not limited in particular, for example, the density at 25 .degree. C. is preferably in a range from 0.6 g/cm3 to 1.0 g/cm3.

The constitution of the volatile solvent including the base is not limited in particular. The volatile solvent may include the base only, or the base and at least one additive. Here, the concentration of the base is not limited in particular, for example, the concentration of the base is preferably in a range from 50 volume % to 100 volume % based upon the total volume of the volatile solvent, more preferably in a range from 80 volume % to 100 volume % based upon the total volume of the volatile solvent. In this way, the effect of the base holding the ozone gas stably is surely shown, and it is possible to expect a strong sterilizing property, a safety and a long-term stability. Meanwhile, when the concentration of the base is less than 50 volume % based upon the total volume of the volatile solvent, the effect of the base may not be expected.

The additive is not limited in particular. For example, the SP value ((cal/cm3) ½) of the additive is in a range from 6.0 (cal/cm3) ½ to 11.0 (cal/cm3) ½, the additive is no reactivity or weak reactivity with the ozone gas and has the boiling point being different from the boiling point of the base preferably. The weak reactivity means that when the volatile solvent obtained by adding the additive to the base is bubbled ozone gas, the additive hardly reacts and exists (not reacting chemically). Here, if the composition of the base is determined, the boiling point of the base is decided. In this way, the compatibility of the additive with the base, and the stability of the additive to the ozone gas can be ensured, and it is possible to control the complete drying time of the volatile solvent in the volatile disinfectant.

The additive can include a non-volatile liquid paraffin, a non-volatile silicone oil, a cyclo methyl hydrogen silicone oil, hydrocarbons, isoparaffins, mineral spirits, etc. The additive of a polar solvent can include a non-cyclic hydrocarbon such as pentane, hexane, heptane, octane, nonane, decane, undecane, dodecane, etc. or a cyclic hydrocarbon such as cyclopentane, cyclohexane, cycloheptane, cyclooctane, etc. The additive of a non-proton type polar solvent can include a halogenated hydrocarbon such as methylene chloride, ethyl chloride, chloroform, carbon tetrachloride, trichlorethylene, etc. or an ether such as dimethyl ether, diethyl ether, butyl ether, tetrahydrofuran (THF), etc. or a ketone such as acetone, methyl ethyl ketone (MEK), methyl-n-butyl ketone (MBK), methylisobutyl ketone (MIBK), cyclopentanone, cyclohexanone, acetophenone, etc. The additive of a proton type polar solvent can include an ester such as methyl acetate, ethyl acetate, acetate-n-butyl, γ-butyrolactone, etc. or a carboxylic acid such as acetic acid, etc. The additive may include a solvent having double bonds, such as isophorone, oleic acid, etc.

The boiling point of the additive is not limited in particular. For example, when it is desired to shorten the complete drying time of the volatile disinfectant, the boiling point of the additive may be less than the boiling point of the base. When it is desired to lengthen the complete drying time of the volatile disinfectant, the boiling point of the additive may be more than the boiling point of the base.

The usage embodiment of the volatile disinfectant is not limited in particular. The volatile liquid paraffin and the volatile silicone oil of the base are full of liquidity, so the volatile disinfectant may be applied directly to an object, sprayed, or immersed. Also, when the volatile disinfectant is impregnated a cloth such as gauze, the cloth may be fixed to an object. And, an aerosol product obtained by filling the volatile disinfectant into an aerosol container (spray container) together with high pressure gas (compressed gas or liquefied gas) may be used. A diluent obtained by diluting the volatile disinfectant may be used as a disinfectant.

The usage field of the volatile disinfectant is not limited in particular. The usage field can include a medical field, a sanitary field, a food field, an agriculture field, a dairy farming field, a fishery field, a mining industry field, an aviation field, a space field, etc. In the medical field, the volatile disinfectant can be preferably used for critical medical instruments, semi-critical medical instruments, or non-critical medical instruments. The critical medical instrument includes blood dialysis machine, blood pump, cardiac catheterization, urinary catheter, surgical medical equipment, circulation medical device, transplantation embedded medical device, needle, etc. The semi-critical medical instrument includes endoscope, medical or dental handpiece, respiratory therapy medical device, anesthesia medical instrument, laryngoscope, endotracheal intubation tube, the body thermometer, surgical forceps, scalpel, surgical scissor, surgical tweezer, etc. The non-critical medical instrument includes bed pan, manchette of sphygmomanometer (cuff), crutch, stethoscope, bed rail, linen, etc. In the sanitary field, the volatile disinfectant can be preferably used for each member of hospital, nursing facility, autopsy body facility, breeding facility of experimental animals, etc. For example, it is most preferable because the solvent does not remain on an autopsy table placing dead body, a breeding cage of laboratory hamster, etc. The volatile disinfectant can be preferably used for antifungal agent, deodorant, bleaching agent, etc. based on a sterilizing property, a deodorizing power, or an oxidation bleaching power of the ozone. In the food field, the volatile disinfectant can be preferably used for each member of food processing facility, etc. or food itself. For example, it is most preferable for the sterilization and the disinfection of a cutting device to cut foods, or pathogens (Sarumorera bacteria, etc.) of destructive fungi including in meat itself by kneading the volatile disinfectant into food such as meat, etc. In the agriculture field, the volatile disinfectant can be preferably used for each member of farm products fabrication plant, etc. Also, the sterilizing property of the ozone has insect-repelling effects, so, the volatile disinfectant can be used for an insect repellent for agriculture, or an insecticide sheet. In dairy farming field, the volatile disinfectant can be preferably used for each member of livestock breeding facilities, livestock fertilizing facilities, etc. For example, it is most preferable for the sterilization and the disinfection of germs in before and after the fertilization in fertilization facilities of livestock such as cattle, horses, pigs, chickens, etc.

<Method for Producing a Volatile Disinfectant>

Next, a method for producing a volatile disinfectant in the present invention is explained. The method for producing a volatile disinfectant in the present invention comprises a step of bubbling ozone gas into a volatile solvent, the volatile solvent containing at least one volatile liquid paraffin selected from the group consisting of a light liquid isoparaffin, a light isoparaffin, and a hydrogenated polyisobutene, one volatile silicone oil consisting of a cyclic dimethyl silicone oil, or a mixture thereof as a base, and a step of stirring the volatile solvent bubbled ozone gas to thereby allow the volatile solvent to contain the ozone gas, the method characterized by producing the volatile disinfectant, when the volatile disinfectant applied to an object, the volatile disinfectant inactivating pathogens on the object and then volatilizes from the object. The method for producing the volatile disinfectant in the present invention is carried out by a producing apparatus shown in FIG. 1. As shown in FIG. 1, the producing apparatus 10 includes a generating part 11, a predetermined container 12, a supplying part 13, and a stirring part 14. The generating part 11 generates ozone gas. The container 12 contains a volatile solvent 12a containing a volatile liquid paraffin, a volatile silicone oil, or a mixture thereof as a base. The supplying part 13 bubbles the ozone gas 12b into the volatile solvent 12a in the container 12. The stirring part 14 stirs the volatile solvent 12a bubbling the ozone gas 12b so as to allow the volatile solvent 12a to contain the ozone gas 12b. And the producing apparatus 10 produces the volatile disinfectant, when the volatile disinfectant is applied to a predetermined object, the volatile disinfectant inactivating pathogens on the object and then volatilizing from the object.

Here, the method that the generating part 11 generates can be used for a silent discharge method, an electrolytic method, an optical reaction method, a high frequency electrolytic method, a solid polymer electrolyte method, etc. The generating part 11 may include ozone bomb enclosing the ozone gas 12b as it is.

The method that the supplying part 13 bubbles the ozone gas 12b can be used for locating the end part 12d of a long supplying tube 12c on the bottom of the volatile solvent 12a as it is, or adopting a diffuser tube 12e of a porous substance releasing an enclosed gas as microbubbles to the end part 12d.

The method that the stirring part 14 stirring the volatile solvent 12a can be used for rotating a predetermined stirring blade 14a at a predetermined rotational speed as shown in FIG. 1, or by rotating a stirrer by using a magnetic force such as a magnetic stirrer. The ozone gas 12b may be stirred and fined by vibrating a predetermined resonator in the volatile solvent 12a, or irradiating ultrasonic waves to the volatile solvent 12a with a predetermined ultrasonic generator.

The concentration of the ozone gas 12b in the volatile solvent 12a is a linear relationship to a bubbling time of the ozone gas 12b, typically, the target concentration of ozone gas 12b (goal concentration) may be obtained by adjusting the bubbling time (sec).

EXAMPLES, COMPARATIVE EXAMPLES, ETC

The present invention will be explained below according to Examples, Comparative examples, etc., and do not limit by there.

Example 1

As one volatile liquid paraffin, an isoparaffinic hydrocarbon (the boiling point is approximately 170 .degree. C., the SP value is 7 (cal/cm3) ½, the density at 25 .degree. C. is 0.755 g/cm3, manufactured by Idemitsu Kosan Co., Ltd.) was selected. The producing apparatus 10 shown in FIG. 1 was used, the volatile disinfectant was produced by bubbling ozone gas into the volatile solvent being the volatile liquid paraffin as a base (the concentration of the base is 100 volume % based upon the total volume of the volatile solvent) at a predetermined time and by stirring the volatile solvent, the concentration of the ozone gas in the volatile disinfectant was 10.0 ppm, the volatile disinfectant was used as a volatile disinfectant of Example 1. In addition, the concentration of the ozone gas in the volatile disinfectant was measured with the measuring equipment (manufactured by Eco-design Co., Ltd.) based on an ultraviolet absorber method.

Example 2

The same conditions as in Example 1 were repeated except that the base was changed from the volatile liquid paraffin to one volatile silicone oil (annular dimethyl silicone oil, the boiling point is approximately 185 .degree. C., the SP value is 8 (cal/cm3) ½, the density at 25 .degree. C. is 0.956 g/cm3, manufactured by Shin-Etsu Chemical Co., Ltd., for cosmetics, KF-995), and the volatile disinfectant produced was used as a volatile disinfectant of Example 2.

Example 3

The same conditions as in Example 1 were repeated except that the base was changed from the volatile liquid paraffin to a mixture of one volatile liquid paraffin and one volatile silicone oil (the concentration of the volatile liquid paraffin is 50 volume % based upon the total volume of the volatile solvent, and the concentration of the volatile silicone oil is 50 volume % based upon the total volume of the volatile solvent), and the volatile disinfectant produced was used as a volatile disinfectant of Example 3.

Example 4

The same conditions as in Example 1 were repeated except that acetone (the boiling point is 56 .degree. C., the SP value is approximately 9 (cal/cm3) ½, manufactured by Wako Pure Chemical Industries, Ltd.) was selected as an additive except the base (the volatile liquid paraffin), the concentration of the base was 83 volume % based upon the total volume of the volatile solvent and the concentration of the additive was 17 volume % based upon the total volume of the volatile solvent, and the volatile disinfectant produced was used as a volatile disinfectant of Example 4.

Example 5

The same conditions as in Example 1 were repeated except that acetone was selected as an additive except the base (the volatile liquid paraffin), the concentration of the base was 98 volume % based upon the total volume of the volatile solvent and the concentration of the additive was 2 volume % based upon the total volume of the volatile solvent, and the volatile disinfectant produced was used as a volatile disinfectant of Example 5.

Example 6

The same conditions as in Example 1 were repeated except that acetophenone (the boiling point is 200 .degree. C., the SP value is approximately 10 (cal/cm3) ½, manufactured by Wako Pure Chemical Industries, Ltd.) was selected as an additive except the base (the volatile liquid paraffin), the concentration of the base was 98 volume % based upon the total volume of the volatile solvent and the concentration of the additive was 2 volume % based upon the total volume of the volatile solvent, and the volatile disinfectant produced was used as a volatile disinfectant of Example 6.

Example 7

The same conditions as in Example 1 were repeated except that 2-octanone (the boiling point is 173 .degree. C., the SP value is approximately 9 (cal/cm3) ½, manufactured by Wako Pure Chemical Industries, Ltd.) was selected as an additive except the base (the volatile liquid paraffin), the concentration of the base was 98 volume % based upon the total volume of the volatile solvent and the concentration of the additive was 2 volume % based upon the total volume of the volatile solvent, and the volatile disinfectant produced was used as a volatile disinfectant of Example 7.

Example 8

The same conditions as in Example 1 were repeated except that cyclohexanone (the boiling point is approximately 156 .degree. C., the SP value is approximately 10 (cal/cm3) ½, manufactured by Wako Pure Chemical Industries, Ltd.) was selected as an additive except the base (the volatile liquid paraffin), the concentration of the base was 98 volume % based upon the total volume of the volatile solvent and the concentration of the additive was 2 volume % based upon the total volume of the volatile solvent, and the volatile disinfectant produced was used as a volatile disinfectant of Example 8.

Example 9

The same conditions as in Example 1 were repeated except that isophorone (the boiling point is approximately 215 .degree. C., the SP value is approximately 10 (cal/cm3) ½, manufactured by Wako Pure Chemical Industries, Ltd.) was selected as an additive except the base (the volatile liquid paraffin), the concentration of the base was 98 volume % based upon the total volume of the volatile solvent and the concentration of the additive was 2 volume % based upon the total volume of the volatile solvent, and the volatile disinfectant produced was used as a volatile disinfectant of Example 9.

Comparative Example 1

The same conditions as in Example 1 were repeated except that the base was changed from the volatile liquid paraffin to non-volatile liquid paraffin (the density at 25 .degree. C. is 0.838 g/cm3, manufactured by MORESCO Co., Ltd., Moresco white P-55), and the disinfectant produced was used as a disinfectant of Comparative Example 1.

Comparative Example 2

The same conditions as in Example 1 were repeated except that the base was changed from the volatile liquid paraffin to non-volatile silicone oil (dimethyl silicone oil, manufactured by Shin-Etsu Chemical Co., Ltd.), and the disinfectant produced was used as a disinfectant of Comparative Example 2.

The disinfectants of Examples 1-9 and Comparative Examples 1, 2 were evaluated in the following.

<Sterilization Test>

At first, *Bacillus subtilis* of a spore forming bacteria said to be the most durable as a target bacteria of the sterilization test was selected. First, 0.113 µL of a cell suspension of the target bacteria was added to 1.0 mL of an aseptic solvent (acetone), the concentration of the cell suspension was diluted. Next, 1.0 mL of the disinfectant was mixed to 0.01 mL of the diluent, and the mixing time (contact time) was 1 minute and 5 minutes. After the contact time passed, 10 µL of sample was taken from the mixture with a bacteria spreader, was spread on a heart infusion agar, and the heart infusion agar was cultured for 24 hours at 35 .degree. C. And, the heart infusion agar was observed whether or not a colony of species of bacteria has been formed on the heart infusion agar, Positive (+) was evaluated when the colony of species of bacteria has been formed, or Negative (−) was evaluated when the colony of species of bacteria has not been formed. The sterilization test for *Bacillus subtilis* was carried out at the time point of the production completion of the disinfectant and the time point after one month passed from the production completion under the conditions that the sterilization was stored in a predetermined container in a sealed state. About *Bacillus coli, Staphylococcus aureus*, and *Pseudomonas aeruginosa*, as common bacterium, the sterilization test at the conditions that the contact time was 5 minutes and the disinfectant at the time point of the production completion was used.

At first, *Candida tropicalis* (pathogen of *Candida disease*) as target fungi (mold) of the sterilization test was selected. First, a fungal suspension was coated on an agar medium for fungal culture using a bacteria spreader, 5.0 mL of the disinfectant was uniformity spread on that, after the disinfectant was contacted with the fungal suspension for 20 minutes, and the agar medium was cultured for 24 hours at 35 .degree. C. And, in the same operations, the agar medium was observed whether a colony of fungi has been formed on the agar medium.

*Feline calicivirus* of an alternative virus of Norovirus as a target virus of the sterilization test was selected, 1.0 mL of the disinfectant was added to a virus suspension of *Feline calicivirus* and worked, a viral infectivity of the worked solution before and after the disinfectant was contacted with the virus suspension for 5 minutes was measured, it is determined whether or not the viral infectivity of the worked solution after 5 minutes has reduced than the viral infectivity of the worked solution at the time point of the working starting. The series of measurements of these were measured by general foundational juridical person food analysis development center.

<Drying Test>

At room temperature, after 1.0 mL of the disinfectant was applied to a test panel of stainless steel, the disinfectant was left at room temperature for one day, and the disinfectant was observed whether or not the applied disinfectant volatilized (dried). When a trace of the disinfectant applied to the test panel became iridescent irregularities (interference fringes) corresponding to volatilizing, it is determined that the disinfectant all volatilized, and, "volatile" was evaluated, or when a trace of the disinfectant applied to the test panel did not become interference fringes, "non-volatile" was evaluated.

<Calculation of Drying Curve>

1 g (approximately 1.5 mL) of the disinfectant on an aluminum cup (the total weight is approximately 0.1 g) of aluminum foil was weighed, the aluminum cup with the disinfectant was left at room temperature, elapsed times from the left time point were measured. And, among the elapsed times, the weight of aluminum cup at a predetermined drying time was weighed, the weight of the remaining disinfectant was calculated by subtracting the weight of the aluminum cup from the weighed weight, the weight (drying weight) of the remaining disinfectant was converted to a percentage by assuming the weight of the disinfectant of the left starting time (0 hour) to be 100%. The drying curve was calculated by repeat that conversion at a plurality of different drying times.

<Safety Test>

An oral cavity mucous membrane irritation test (guinea pig) and an acute oral toxicity test (mouse) about the disinfectant were carried out by general foundational juridical person food analysis development center.

<Result>

As shown in FIG. 2, in the sterilization test of *Bacillus subtilis*, the disinfectants of Examples 1-9, Comparative Examples 1, 2 at the time point of the production completion showed Negative (−), and it is found that the disinfectants can inactivate even a high durable pathogen. And, the disinfectants of Examples 1-9 after one month passed inactivated *Bacillus subtilis*. In the sterilization test of *Bacillus coli, Staphylococcus aureus, Pseudomonas aeruginosa, Candida tropicalis*, the disinfectants of Examples 1-9 inactivated all pathogens.

For example, only a volatile liquid paraffin was contacted with the diluent of *Bacillus subtilis*, the contact times were set to less than 1 minute, 1 minute, 5 minutes, 10 minutes, 20 minutes, and 30 minutes, the sample were spread on an agar medium, then the agar medium was cultured for 24 hours at 35 .degree. C. as the above sterilization test. As shown in FIG. 3A, in any contact times, *Bacillus subtilis* cultivated, and Positive (+) were shown. Meanwhile, the disinfectants of Example 1 was contacted with the diluent of *Bacillus subtilis*, the contact times were set to less than 1 minute, 1 minute, 5 minutes, 10 minutes, 20 minutes, and 30 minutes, the sample were spread on an agar medium, then the agar medium was cultured for 24 hours at 35 .degree. C. as the above sterilization test. Then, as shown in FIG. 3B, in any contact times, *Bacillus subtilis* were inactivated and no-cultivated, and Negative (−) were shown.

Figure 4:
FIG. 4 is a photograph indicating an agar medium after the culture when a volatile disinfectant of Example 1 was contacted with a diluent of *Bacillus coli, Staphylococcus aureus*, or *Pseudomonas aeruginosa* for 5 minutes.
Figure 5:
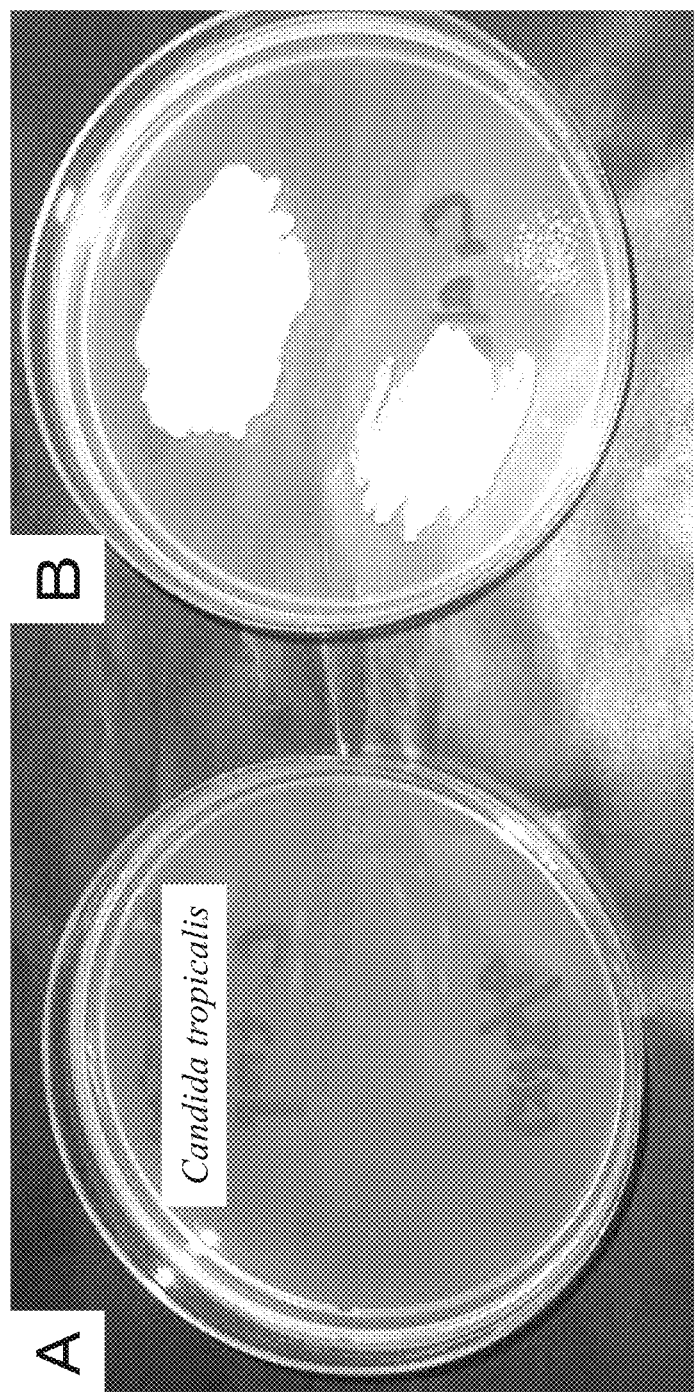
FIG. 5A is a photograph indicating an agar medium after the culture when a volatile disinfectant of Example 1 was contacted with a suspension of *Candida tropicalis* for 20 minutes.
FIG. 5B is a photograph indicating an agar medium after the culture when only a volatile liquid paraffin was contacted with a suspension of *Candida tropicalis* for 20 minutes.

As shown in FIG. 4, the disinfectants of Example 1 was contacted with each of *Bacillus coli, Staphylococcus aureus*, and *Pseudomonas aeruginosa* for 5 minutes, the samples were cultured on agar mediums, thus, the Bacterium were inactivated, and Negative (−) were shown. As shown in FIG. 5A, when the disinfectants of Example 1 was contacted with *Candida tropicalis* for 20 minutes, the fungus were inactivated, and Negative (−) were shown. As shown in FIG. 5A, when only a volatile liquid paraffin was contacted with *Candida tropicalis* for 20 minutes, the fungus cultivated.

In the disinfectant of Example 1 of the sterilization test of *Feline calicivirus*, the viral infectivity of the worked solution at the time point of the working starting was 7.3 (logTCID50/mL), and the viral infectivity of the worked solution after 5 minutes was 5.5 (logTCID50/mL). The TCID50 means 50% tissue culture infective dose. Therefore, it is found that the viral infectivity was reduced by working the disinfectant of Example 1 to *Feline calicivirus*.

Figure 6:
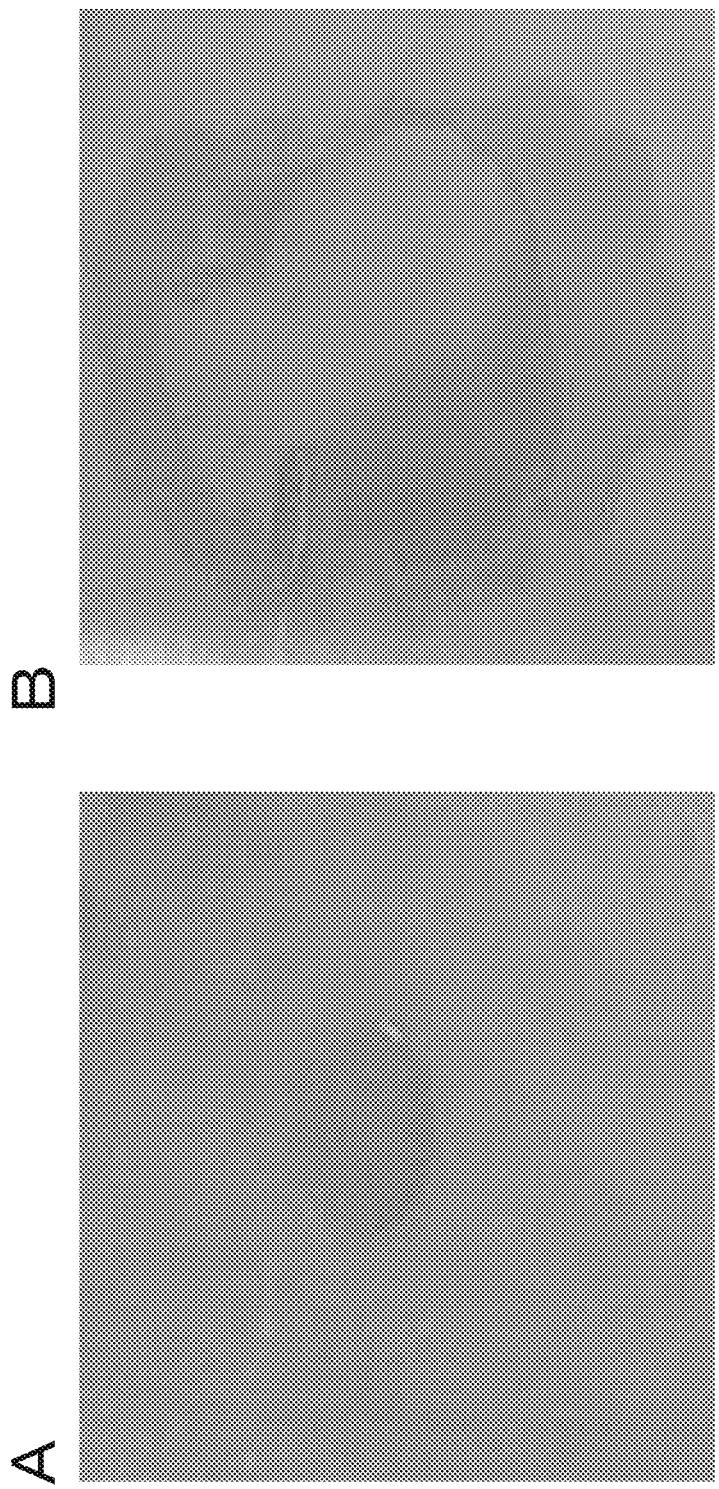

As shown in FIG. 2, in the drying test, the disinfectants of Examples 1-9 showed "volatile", and the disinfectants of Comparative Examples 1, 2 showed "non-volatile". When 1.0 µL of the disinfectant of Example 1 was dropped on the test panel of stainless steel and the disinfectant was left for a few minutes as shown in FIG. 6A, as shown in FIG. 6B, by the disinfectant of Example 1 volatilizing, an interference fringes appeared and the solvent did not remain.

Figure 7:
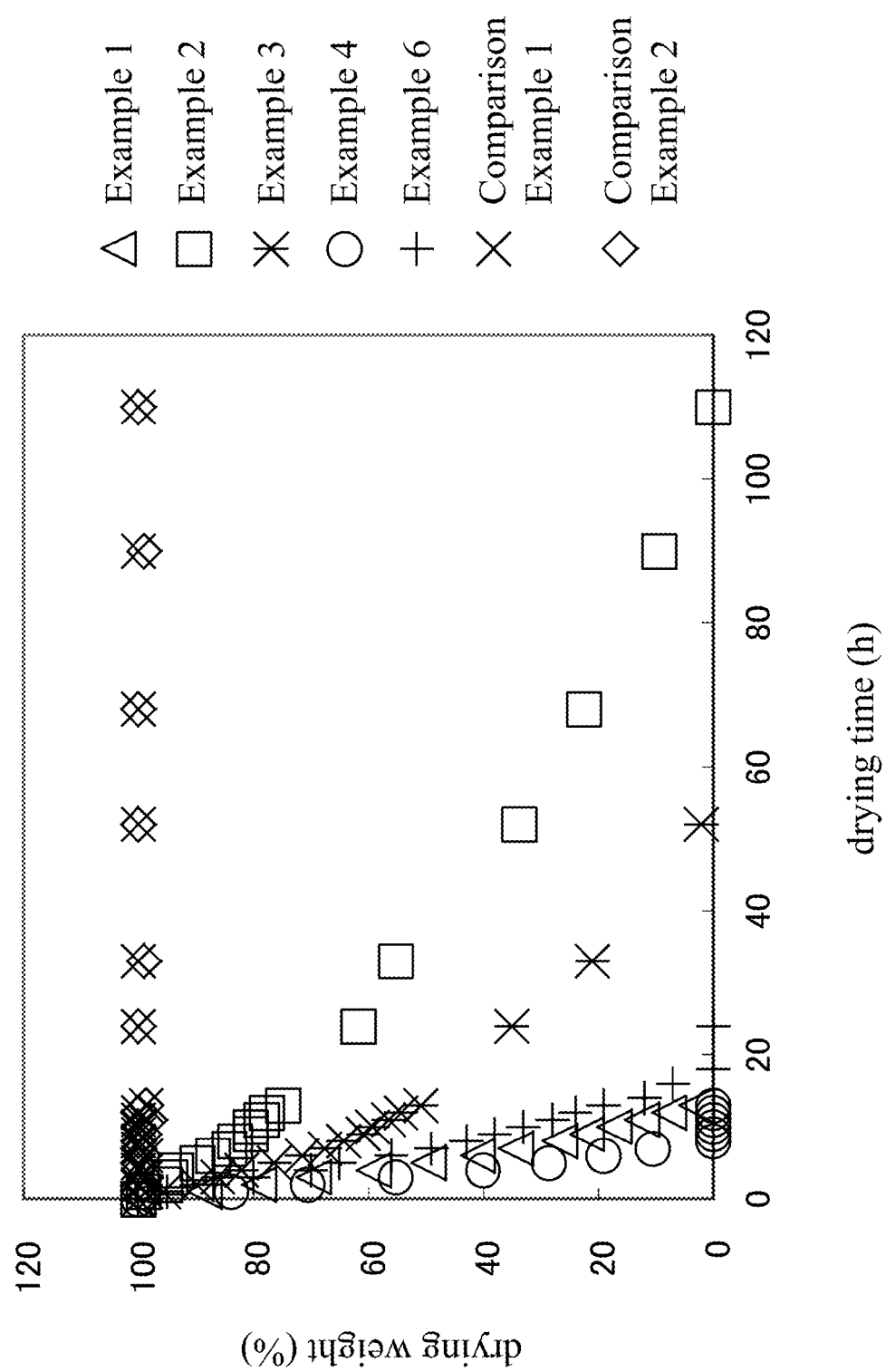
FIG. 7 is a view indicating a drying curve in accordance with Examples 1-4, 6 and Comparison Examples 1, 2.

As shown in FIG. 7, it is found that in the drying curve of Examples 1-4, 6, when a predetermined drying time passed, the drying weight was approximately 0% and the disinfectant dried. It is found that each of the volatile disinfectants of Examples 1-4, 6 have a different complete drying time. Meanwhile, it is found that in the drying curve of Comparative Examples 1, 2, the drying weight was always approximately 100% and the disinfectant did not dry. In view of the above sterilization test, it can be confirmed that after the disinfectants of Examples 1-9 inactivate pathogens on a predetermined object, and then the disinfectants volatilize from the object. As shown in the drying curves of Examples 1-3, by changing the mixing ratio of the volatile liquid paraffin and the volatile silicone oil, it is found that it is possible to adjust the complete drying time. As shown in the drying curves of Examples 4, 6, by adding an additive having a low boiling point (acetone) or an additive having a high boiling point (acetophenone) to the volatile liquid paraffin, it was found that it is possible to control the complete drying time.

In the oral cavity mucous membrane irritation test of the safety test, it was the result that the disinfectants of Examples 1 and 2 have no irritation to oral mucosa of guinea pig. In the acute oral toxicity test of the safety test, it was the result that LD50 value of the disinfectants of Example 1, 2 in a single oral administration using a mouse is more than 2000 mg/kg in both sexes, and the abnormality of the mouse was not seen.

INDUSTRIAL APPLICABILITY

As described above, a volatile disinfectant, and a method for producing a volatile disinfectant in the present invention are useful as a disinfectant for sterilization, pasteurization, and disinfection of all fields such as a medical field, a sanitary field, a food field, an agriculture field, a dairy farming field, a fishery field, a mining industry field, an aviation field, a space field, etc. It is effective as a volatile disinfectant and a method for producing a volatile disinfectant in the present invention, which can inactivate even a high durable pathogen, make a post-processing after the application unnecessary, and improve the safety for user to treat.

REFERENCE SIGNS LIST

10 Producing apparatus
11 Generating part
12 Container
12*a* Volatile solvent
12*b* Ozone gas
13 Supplying part
14 Stirring part

The invention claimed is:
1. A volatile disinfectant, consisting of:
a volatile liquid paraffin and one additive,
wherein the volatile liquid paraffin and the additive contain ozone gas bubbled thereinto under stirring the volatile liquid paraffin and the additive to thereby allow the volatile liquid paraffin and the additive to contain the ozone gas,
wherein the volatile liquid paraffin is an isoparaffinic hydrocarbon,
wherein the boiling point of the volatile liquid paraffin is 170 .degree. C.,
wherein the density at 25 .degree. C. of the volatile liquid paraffin is 0.755 g/cm$^3$,
wherein the boiling point of the additive is less than the boiling point of the volatile liquid paraffin,
wherein the concentration of the volatile liquid paraffin is in a range from 50 volume % to 98 volume % based upon the total volume,
wherein the additive is a polar solvent and is selected from the group consisting of dimethyl ether, diethyl ether, butyl ether, tetrahydrofuran (THF), acetone, methyl ethyl ketone (MEK), methyl-n-butyl ketone (MBK), methylisobutyl ketone (MIBK), cyclopentanone, cyclohexanone, methyl acetate, ethyl acetate, acetate-n-butyl, and acetic acid,
wherein when the volatile disinfectant applied to an object, the volatile disinfectant inactivates pathogens on the object and then volatilizes from the object.

2. The volatile disinfectant of claim 1, wherein:
the additive is selected from the group consisting of dimethyl ether, diethyl ether, tetrahydrofuran (THF), acetone, methyl ethyl ketone (MEK), methyl acetate, and ethyl acetate.

* * * * *